United States Patent [19]
Wilson et al.

[11] Patent Number: 5,116,384
[45] Date of Patent: May 26, 1992

[54] PROSTHETIC FOOT

[75] Inventors: Michael T. Wilson, Missouri City, Tex.; David F. Jolly, Abrams, Wis.

[73] Assignee: Syncor, Ltd., Abrams, Wis.

[21] Appl. No.: 576,228

[22] Filed: Aug. 31, 1990

[51] Int. Cl.⁵ ............................... A61F 2/66
[52] U.S. Cl. ........................ 623/49; 623/50; 623/53; 623/55
[58] Field of Search ................. 623/48–49, 623/53–56, 47, 50–52

[56] References Cited

U.S. PATENT DOCUMENTS

| | | | |
|---|---|---|---|
| 409,311 | 8/1889 | Snyder | 623/53 X |
| 419,019 | 1/1890 | Kolbe | 623/54 X |
| 1,071,230 | 8/1913 | Hanger | 623/54 X |
| 1,294,632 | 2/1919 | Dickson | |
| 3,196,463 | 7/1965 | Farneth | 623/49 |
| 4,328,594 | 5/1982 | Campbell et al. | |
| 4,446,580 | 5/1984 | Furuya et al. | 623/53 |
| 4,461,045 | 7/1984 | Shorter et al. | |
| 4,463,459 | 8/1984 | Shorter et al. | |
| 4,547,913 | 10/1985 | Phillips | 623/27 |
| 4,645,509 | 2/1987 | Poggi et al. | 623/55 |
| 4,721,510 | 1/1987 | Cooper et al. | 623/55 |
| 4,822,363 | 4/1989 | Phillips | 623/27 |
| 5,030,239 | 7/1991 | Copes | 623/52 |

FOREIGN PATENT DOCUMENTS

| | | | |
|---|---|---|---|
| 1391643 | 4/1988 | U.S.S.R. | 623/53 |
| 8400681 | 3/1984 | World Int. Prop. O. | 623/54 |

OTHER PUBLICATIONS

Hosmer, The Quantum Foot—Brochure.
Campbell-Childs, Inc. Stationary Attachment Flexible Endoskeleton II Mailer, Jul. 1989.
Campbell-Childs, Inc.—S.A.F.E. Prosthetic Foot Catalog.
United States Manufacturing Company—Multiplex Brochure.
The Ohio Willow Wood Co., Step into the Future with the Carbon Copy II Energy Storing Foot.
Footnotes (Flex-Foot)—Mailer, Mar. 1989.
Flex-Foot, Inc.—Price List.

*Primary Examiner*—Randall L. Green
*Assistant Examiner*—David H. Willse
*Attorney, Agent, or Firm*—Arnold, White & Durkee

[57] ABSTRACT

A prosthetic foot comprises a flexible planter member, a flexible dorsal member, and a posterior pylon member connected by ball and socket joints. Elastic snubbers and torsion resistors aid in controlling the movement of the three structural members relative to each other. During ambulation, the foot deforms elastically to generate approximately the same forces and feel to the user as would be generated by the skeleton, muscles, tendons, and ligaments of a natural foot.

20 Claims, 3 Drawing Sheets

PROSTHETIC FOOT

BACKGROUND OF THE INVENTION

A. Field of the Invention

The present invention is for a prosthetic foot having a flexible plantar member, a flexible dorsal member, and a posterior pylon member connected by ball and socket joints. Elastic snubbers and torsion resistors are positioned in between the plantar member and the dorsal member to aid in controlling the movement of the three structural members relative to each other. During ambulation, the design of the foot including the various ball and socket joints combined with the various elastic members function to allow the foot to deform elastically to generate approximately the same forces and feel to the user as would be generated by the skeleton, muscles, tendons, and ligaments of a natural foot.

B. Description of the Related Art

Artificial limbs and particularly prosthetic feet and legs have been known for centuries. The earliest were probably similar to the crude wooden "peg legs." These early devices enabled the user to stand and to walk awkwardly, usually with the additional aid of a crutch or cane.

In the early 20th century designers of artificial or prosthetic feet first attempted to duplicate the appearance and function of a natural foot. During the ensuing 70 or 80 years, the designs for prosthetic feet have remained relatively unchanged. What changes did occur seemed to come mainly from improvements in available materials. Classic prosthetic feet used spring principles to cushion shocks due to walking and running and allow some degree of movement of the foot. U.S. Pat. No. 1,294,632 to Dickson discloses such an artificial foot. More versions of the spring foot also known as an energy storing foot, are disclosed in U.S. Pat. No. 4,547,913, 4,645,509, and 4,822,363.

These devices have come to be known as energy storing feet because as the springs are deflected they store energy which is largely returned to the user as the foot elastically returns to its undeformed shape. The obvious disadvantages to such prosthetic devices are that springs alone poorly duplicate the deflections, forces, and feel to the user of a natural foot.

Designers have attempted to more closely approximate the action of a natural foot by adding ball and socket ankle joints geometrically similar to a natural anatomical ankle. Feet incorporating simulated ankle joints do theoretically allow for more natural movement, but copying the anatomical joint itself is not enough. Without all of the muscles, tendons, and cooperating bone structure of an anatomical foot, the anatomical type ankle joint is too unstable to be practical. Attempts to stabilize prosthetic ball and socket ankle joints are shown in U.S. Pat. Nos. 4,461,045 and 4,463,459, both issued to Shorter et al.

SUMMARY OF THE PRESENT INVENTION

The present invention radically departs from the known prior art by placing the prosthetic ankle joint at the bottom of the prosthetic foot rather than trying to simulate the natural anatomical ankle joint geometry. The prosthetic ankle joint shown herein is a ball and socket or more correctly a modified ball and socket joint. It is understood that other universal couplings can be used to simulate ankle movement and this invention is not limited to having ball and socket joints. Lowering the ankle joint to the bottom of the foot provides a tremendous increase in stability. In anatomical ankle joints, there is a tendency of the ankle joint to buckle, but this tendency is resisted by powerful leg muscles and tendons. Prosthetic feet which simulate the anatomical joint do not benefit from the stability provided by muscles, tendons and ligaments and, therefore, present an awkward buckling problem for the user. Lowering the prosthetic ankle joint to the base of the prosthetic foot reduces the moment around the joint and the resulting tendency to buckle to virtually zero.

In order to allow movement of the prosthetic foot that will approximate the movement of a natural foot, the invention includes secondary and tertiary ball joints. These bal joints assist in allowing inversion and eversion of the foot, but, because of the overall foot design, do not allow ankle buckling. The foot further comprises flexible plantar and dorsal members which combine the anatomical functions of natural foot muscles and skeleton. These members are connected by the socket joints and their relative motion can be controlled by elastic dampers, all of which will be described in more detail in the detailed description of the preferred embodiment.

In a natural foot, rigidity and flexibility are provided by the skeleton, which acts as a frame, and the surrounding muscles, tendons and ligaments which control movement. The individual bones of the skeleton are relatively rigid and inflexible so movement is provided for by interconnection of multiple bones joined together. The natural foot is held in shape yet allowed to flex and move for walking, running, and other human activity by muscles, tendons, and ligaments. In a natural foot, the muscles have a certain amount of inherent flexibility, but operate mainly by being contracted and relaxed by the brain. The instant invention simulates the combination of muscles and skeleton by use of a roughly triangular shaped skeleton whose members have designed-in flexibility and damping to simulate muscle action. The geometry of the structural members does not attempt to reproduce the geometry of a natural foot, as has been done by prior art, because lack of muscle control in a prosthetic foot requires entirely different structural considerations.

The combination of ball joints, rigid anterior pylon, flexible plantar and dorsal members, and interconnecting motion resisting dampers closely simulates the action and feel to the user of a natural foot. The combination provides a tremendous improvement over the prior art which used various configurations of leaf springs to allow movement.

DETAILED DESCRIPTION OF A PREFERRED EMBODIMENT

Figure 1:
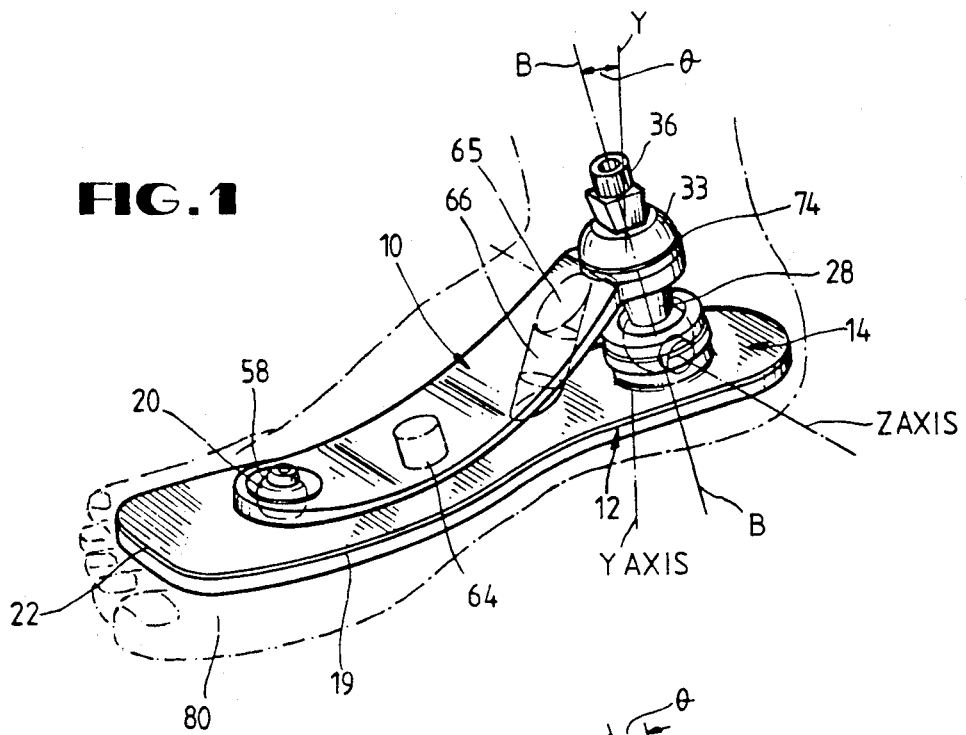
FIG. 1 is a perspective side view showing the invention with the cosmesis which surrounds it shown by phantom lines.
Figure 2:
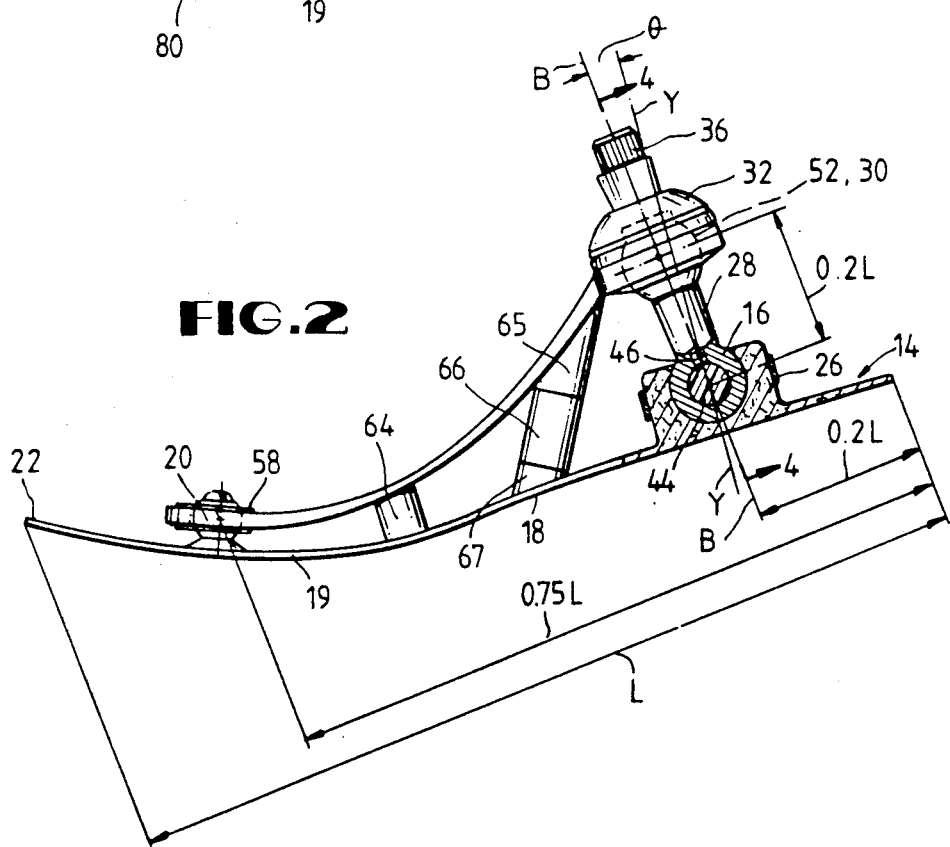
FIG. 2 is a side view of the invention shown without the cosmesis and with the bottom rear quarter cut away to show the primary ball and socket joint.

Refer first to FIGS. 1 and 2. The prosthetic foot 10 is built on a flexible plantar member 12 with a heel portion 14, a primary socket 16, an arch portion 18, a ball portion 19, including a tertiary ball 20, and a toe portion 22. The size of the plantar member 12 varies according to individual user needs. In order to describe geometric relationships of various members of the foot 10, the plantar member will be referred to as having a length "L". Other dimensions will then be referred to as being some percentage of the length L.

In experimental models, plantar members have been constructed of fiberglass and carbon fibers embedded in epoxy resins. The plantar member 12 serves the same function as the keel of a ship and the remaining components are built using it as the base. A particularly successful prosthetic foot 10 employed a plantar member 12 made of unidirectional glass fibers running along the length of the foot 10 and embedded in Hexcel 2316 semirigid epoxy. Fiberglass material weighing 13.8 ounces per square yard was laminated nine layers thick at the arch portion 18 and tapered to four layers thick at the heel portion 14 and toe portion 22. Models have been made using plantar members approximately 1½ to 2¼ inches wide at the heel and toe portions with an hourglass-shaped taper into the arch portion of about 1 to 1½ inches in width as shown in FIG. 1. The actual physical dimensions of the foot depend on the size of the patient to be fitted, but the hourglass configuration has been shown to help approximate the correct flexural feel during use.

Between the heel portion 14 and the arch portion 18 is located a primary socket 16 which is molded in place around a primary ball 24. The primary socket 16 is located approximately 20% of the length (L) of the plantar member 12 from its rearmost edge. The primary socket 16 is located as near the bottom of the plantar member 12 as is structurally feasible to increase stability and reduce buckling of the related joint. For added strength and rigidity, the primary socket 16 is surrounded by a cylindrical steel band 26.

Still referring to FIGS. 1 and 2, a rigid posterior pylon 28 which terminates on its lower end in the previously mentioned primary ball 24 may be seen. The pylon 28 extends upward and inclines toward the toe portion 22 of the foot 10 at an angle Θ of approximately 15 degrees from a vertical y-axis extending from the foot to the user's anatomical knee joint (not shown). The angle Θ may be varied to accommodate the physical characteristics of individual users. The pylon 28 includes a secondary ball 30. The center of the secondary ball 30 is located above the center of primary ball 24 a distance of approximately 20% of the total length (L) of the plantar member 12. The pylon 28 terminates above the secondary ball 30 in a configuration adapted to receive a commercially available adaptor 32 that enables the prosthetic foot 10 to be connected to a prosthetic leg member (not shown). The pylon 28 and balls 24, 30 are subject to extreme loads during use and experimental models have been machined from solid billets of high strength aluminum alloy. Commercial models may use cast or forged titanium alloy pylons and balls to keep weight and cost as low as possible while achieving the necessary strength.

Figure 4:
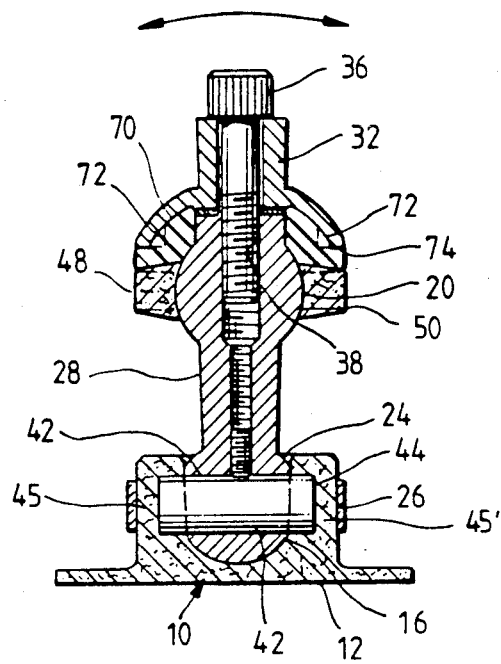
FIG. 4 is a section of the invention shown in FIG. 2 as viewed from the rear.
Figure 5:
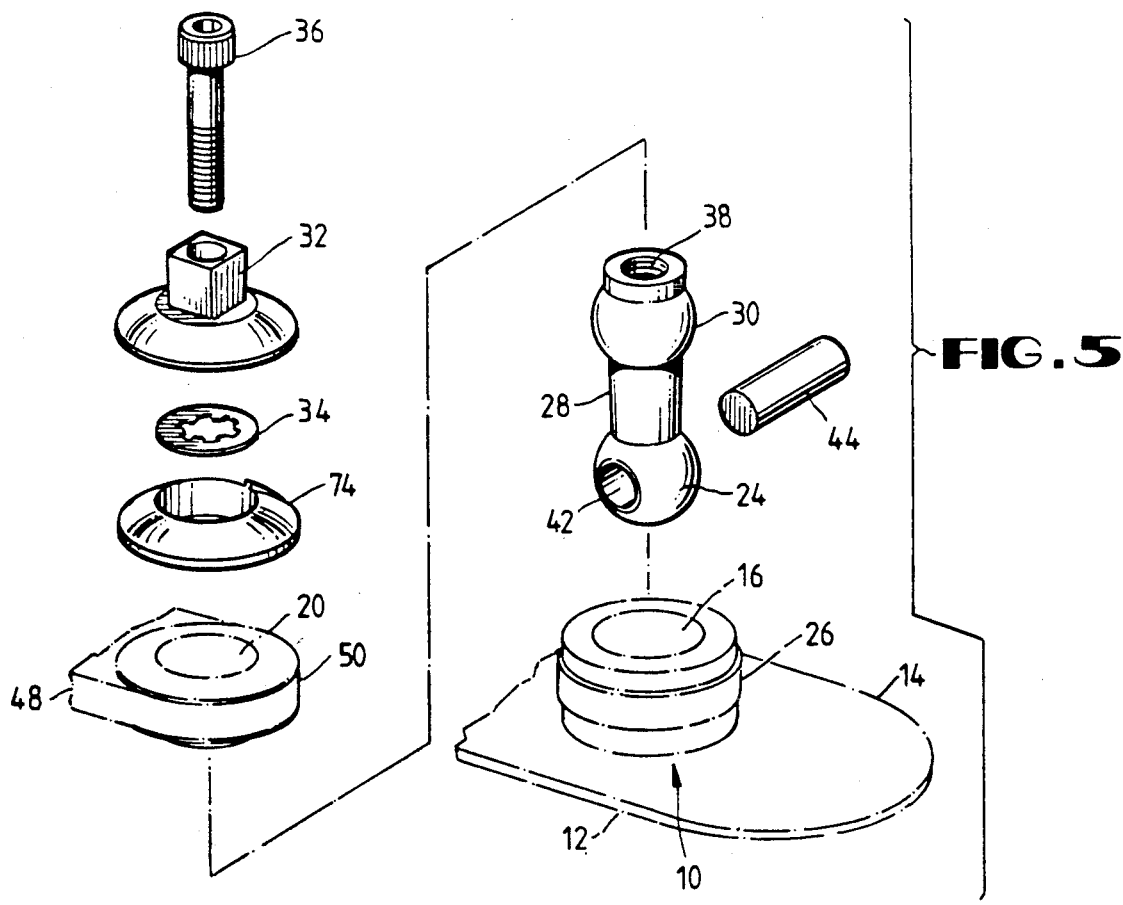
FIG. 5 is an exploded view of the posterior portion of the invention showing the relationship of the heel, the pylon, the primary and secondary ball joints, and the adaptor.

For a complete understanding of the relationship of the pylon 28, the primary and secondary joints, and the adaptor 32 refer also to details shown by FIGS. 4 and 5. The particular adaptor 32 shown and found to be most satisfactory in use is an Endoskeletal Foot Adaptor manufactured by Otto Bock in West Germany. The adaptor 32 fits over the pylon 28 and is held in place by a lock washer 34 and a bolt 36 threaded into the pylon 28.

Below the bolt 36, the pylon 28 is hollow and a threaded hole 38 extends down through the pylon 28 along its longitudinal axis B—B. A second cylindrical hole 42 extends transversely through the primary ball 24. A cylindrical primary antirotational damper 44 extends through the hole 42 and into recesses 45, 45' in each side of the primary socket 16. The primary antirotational damper 44 is made of rubber, neoprene, or high density urethane. It operates to pin the ball 24 in socket 16 and allow rotation only about the horizontal z axis which is transverse to the longitudinal y axis of the foot 10. Because the damper 44 is not rigid but made of resilient material, a very limited rotation of the ball 24 about the x and y axes is also allowed. The damper 44 elastically resists rotation about the x and y axes and tends to return the ball 24 to its initial position with respect to these axes whenever it is moved by external forces. A threaded screw 46 can be screwed into the threaded hole 38 to compress the damper 44 and alter its elastic characteristics. As screw 46 is tightened, it extends into the damper 44 compressing it into the confined space of hole 42 and causing it to become more rigid and resistant to motion. Screw 46 is preadjusted to the required characteristics of a particular individual before bolt 36 is inserted to clamp the adaptor 32 in place.

Figure 3:
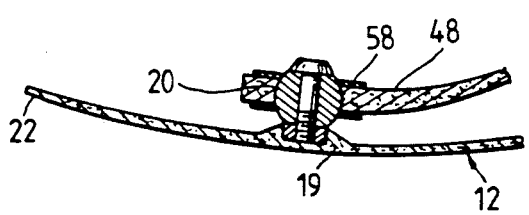
FIG. 3 is a partial side view of the toe area cut away to show the tertiary ball and socket joint.

Referring now back to FIGS. 1 and 2, extending from the secondary ball 30 of the pylon 28 to the toe portion 22 of plantar member 12 is a curved flexible dorsal member 48. The dorsal member 48 includes a rigid anterior portion 50 with a socket 52 to receive ball 30 and form a secondary ball and socket joint (30, 52). The dorsal member 48 extends forward in a flexible anterior portion 56 (see FIG. 6A) to a tertiary socket 58 which receives tertiary ball 20 rigidly attached to the plantar member 12 between the toe portion 22 and the arch portion 18. The center of tertiary ball and socket joint (20, 58) is located approximately 0.75L (75% of the total length L of the plantar member 12) from the rear edge of the plantar member 12. Refer to FIG. 3 for a cross-sectional detail of the tertiary ball and socket joint.

Experimental modes of the foot 10 have used dorsal members 48 made of the same basic materials and construction as the corresponding plantar members 12. One successful model uses a dorsal member with six layers of unidirectional glass fiber cloth. The fibers extend from the front of the member 48 to the rear and are bonded in a base material of Hexcel 2316 semirigid epoxy.

In addition to the ball and socket joints, plantar member 12 is connected to dorsal member 48 by an elastic snubber 64 and an elastic shear reducer 66. The snubber 64 is made of rubber, high density urethane, or other elastic material and is bonded to the plantar member 12 between the arch 18 and the ball and socket joint (20, 58). It extends upward to contact the dorsal member 48. The purpose of the snubber 64 is to act as a compression member so that a downward deflection of dorsal member 48 will transmit force via the snubber 64 into the plantar member 12, thereby increasing the overall stiffness of the foot 10. A downward deflection of plantar member 12 does not transmit force into the dorsal member 48 because in the preferred embodiment the snubber 64 is not bonded to dorsal member 48 and cannot be placed in tension. This causes a unique asymmetric resistance to bending of the foot. The foot is stiffer in resistance to forces and moments which tend to deflect dorsal member 48 downward with respect to plantar member 12 than in resistance to forces and moments which tend to deflect dorsal member 48 upward with respect to plantar member 12. The amount of asymmetry can be varied by changing the size, shape, and elastic modulus and location of snubber 64.

Experimental model which have exhibited particularly good characteristics of feel, locate a cylindrical snubber 64 having a Shore hardness of about 140 approximately 3½ inches behind the tertiary ball and socket joint (58, 20). Sniffness has been varied by changing the snubber diameter from ½ inch to 9/16 inch to ⅝ inch.

The shear reducer 66 is an elongated member also made of rubber, high density urethane, or other similarly stiff elastic material which extends from the rigid anterior portion 50 of dorsal member 48 down and forward to the arch portion 18 of plantar member 12. More rigid members of the shear reducer may be made of materials identical to those of the rigid anterior portion 50 of dorsal member 48 and of the rigid arch portion 18 of plantar member 12. As such, these two additional members (as shown in FIG. 2 as supports 65 and 67, respectively) provide contact structures for the elongated elastic member 66. The purpose of shear reducer 66 is to absorb impact forces generated at secondary ball and socket joint (30, 52) which tend to push dorsal member 48 forward and shear the tertiary ball and socket joint (20, 58). Models with and without shear reducer 66 have been tested and the life of ball and socket joint (20, 58) is significantly improved by the presence of the shear reducer 66.

Finally, referring to FIG. 4, the endoskeletal foot adaptor 32 includes a recess 70 and an internal web 72. The recess is filled with a molded elastic material such as rubber or high density urethane. The elastic material extends slightly below the recess and forms an elastic cushion 74 between the adaptor 32 and the dorsal member 48. The cushion 74 is bonded to the rigid portion 50 of member 48. By means of the bonding and the web 72, rotation of the adaptor 32 with respect to dorsal member 48 is elastically resisted. This allows for the slight rotation of the foot 10 relative to the leg (not shown) of the user which is necessary for simulation of natural walking. In its final form, the entire skeletal framework is preferably covered by a cosmesis 80 made of expanded PVC or polyethylene so that the prosthetic foot has the cosmetic appearance of a natural foot.

OPERATION OF THE PROSTHETIC FOOT INVENTION

Figure 6C:
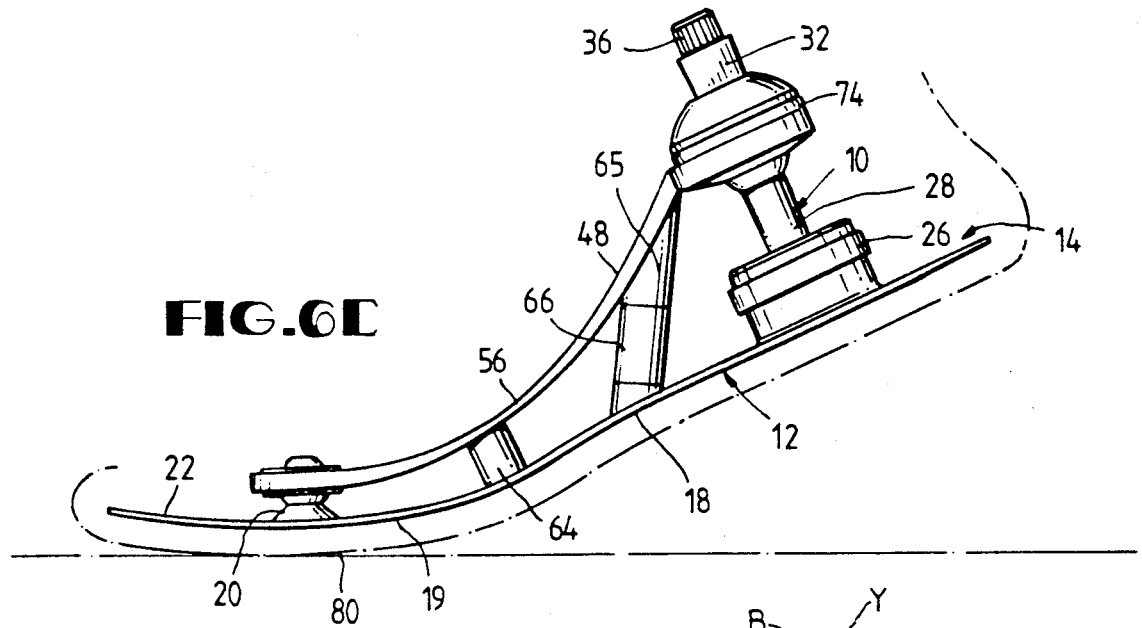
FIG. 6C is a side view of the invention shown near the end of a step just as all the weight is transferred to the toe area.

The operation of the prosthetic foot 10 will be detailed through one step of the user starting with heel strike. Refer now to FIG. 6A. At heel strike the cosmesis 80 contacts the ground and transmits force to heel 14 of the plantar member 12. The heel portion 14 flexes upward absorbing the impact of the heel strike and storing energy to return the foot 10 to its relaxed position. As the heel portion 14 deflects the resultant forces produce a moment about the primary ball and socket joint and the plantar member 12 tends to rotate around the z axis with respect to the pylon 28. Slight rotation occurs but is resisted by tension in dorsal member 48. The floor reaction at the heel 14 also creates a downward distortion of the plantar member 12 between the primary ball and socket joint (24, 16) and the tertiary ball and socket joint (20, 58). The snubber 64 and the shear reducer 66 tend to separate slightly from their respective supports. Downward distortion of the plantar member 12, tension in dorsal member 48, and related slight rotation of the three ball and socket joints simulates natural plantar flexion.

Figure 6B:
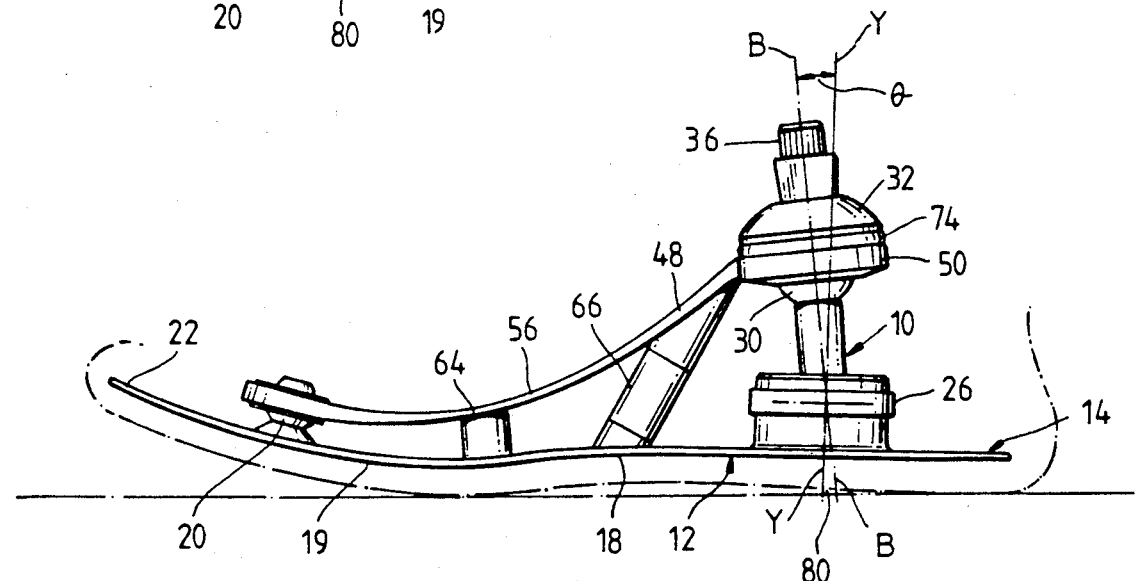
FIG. 6B is a side view of the invention shown during the middle of a step as weight is transferred from the heel to the ball area.
Figure 6A:
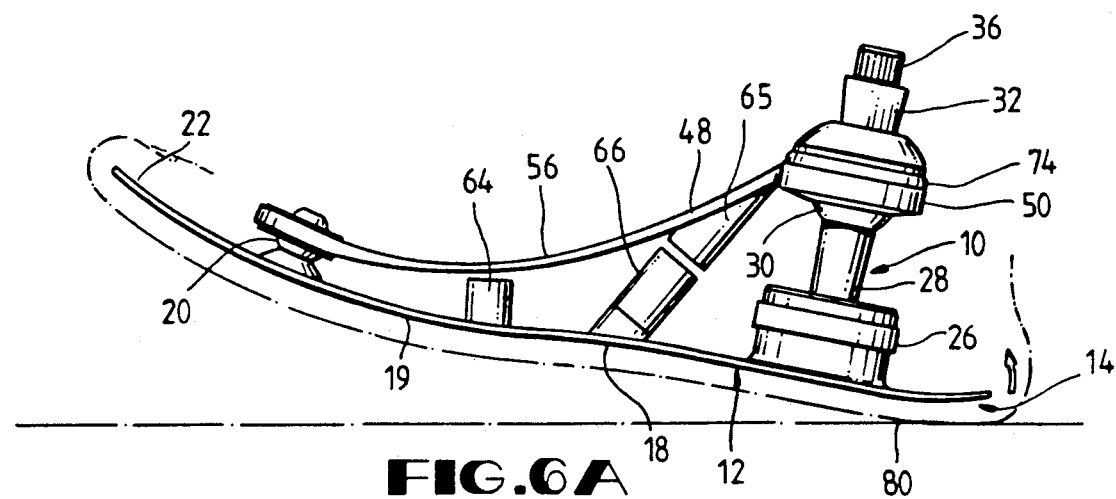
FIG. 6A is a side view of the invention shown as the heel contacts the ground during a step.

Refer now to FIG. 6B. As the user approaches midstance, the heel portion returns to normal relaxed shape and the user's weight is gradually transmitted to the area under the primary ball 24 and socket 16 and the ball portion 19. Also at approximately mid-stance, the moment between the pylon 28 and the plantar member 12 decreases to zero and the tension on the dorsal member 48 is eliminated. The foot 10 returns to essentially its relaxed position and snubber 64 and shear reducer 66 again contact their supports.

As the step continues, load is transferred to the ball portion 19 of the foot 10 and the pylon 28 tends to rotate counterclockwise around the z axis with respect to the plantar member 12. This reverses the earlier moment and dorsal member 48 is placed in compression and tends to flex downward with respect to plantar member 12. This combination of forces and moments places shear reducer 66 in compression reducing the load in the x direction that would otherwise be transmitted to the tertiary ball and socket joint (20, 58).

As the dorsal member 48 tends to deflect downward with respect to the plantar member, it compresses snubber 64 and transfers load into the plantar member 12, thereby increasing the overall stiffness and energy absorbing ability of the foot 10. Simultaneously, normal rotation of the hips of the user during a step rotates the user's leg slightly around the y-axis. This rotation is allowed but resisted elastically by the elastic cushion 74 and the primary antirotational damper 44 allowing the foot to remain stationary relative to the y axis. Without the ability to compensate for this slight rotation of the hips, the foot 10 would also rotate at this crucial point in the step transmitting an unnatural feeling torque from the floor to the user's leg. Also, because the axis B—B of the pylon 28 is angled relative to the vertical y-axis, the rotation about the pylon also causes an inversion moment of the foot around the x axis. This moment is also elastically resisted by the antirotational damper but movement is allowed to a slight extent by the primary and secondary ball and socket joints. This further enhances the natural feel and movement of the foot 10 during the step.

Now refer to FIG. 6C. As the step progresses, all of the weight is transmitted to the toe portion 22 of the plantar member 12 causing the toe to bend upward and further increasing the stresses on the dorsal member 48, the shear reducer 66, and the snubber 64.

Finally at toe off, the elastic stresses stored in the foot 10 cause it to again return to its undeformed shape and in doing so release the stored energy to push the user through the step.

Throughout the entire step cycle from heel contact to toe off, the plantar member 12 and dorsal member 48 act simultaneously and instantaneously, providing a smooth transition of torque through the primary and secondary ball and socket joints.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, while a preferred embodiment of the invention utilizes ball and socket joints at several positions in the prosthetic device, the joints could equally as well be designed using any of a number of such universal joints known to those of skill in the art. All such modifications are intended to be included within the scope of the appended claims.

What is claimed is:

1. A prosthetic foot, comprising:
    a plantar member having first and second end portions, a primary socket connected to said plantar member adjacent said first end portion with said primary socket further positioned closely to a bottom horizontal surface of said plantar member, and a tertiary ball connected to said plantar member adjacent said second end portion;
    a pylon having a first and second end, a primary ball attached to said first end of said pylon, a secondary ball attached to said pylon spaced from said primary ball, and an adaptor assembly attached to said second end of said pylon, said pylon being connected to said plantar member by said primary socket engaging said primary ball; and,
    a dorsal member having first and second end portions, a secondary socket connected to said dorsal member adjacent said first end portion of said dorsal member and a tertiary socket connected to said dorsal member adjacent said second end portion of said dorsal member, said dorsal member being connected to said pylon by said secondary ball engaging said secondary socket, and said dorsal member being connected to said plantar member by said tertiary socket engaging said tertiary ball.

2. A prosthetic foot as in claim 1, wherein said dorsal and plantar members are flexible and said pylon is rigid.

3. A prosthetic foot as in claim 1, further comprising at least one snubber member adhesively attached to said plantar member at points spaced from said balls and sockets, which snubber member, upon downward deflection of said dorsal member transmits force via said snubber member into the plantar member, thereby increasing overall stiffness of said prosthetic foot.

4. A prosthetic foot as in claim 1, further comprising a shear reducer member connected to said dorsal member adjacent said secondary socket and connected to said plantar member at a point approximately midway between said primary socket and said tertiary ball.

5. A prosthetic foot as in claim 3, wherein said snubber member is at least partially made of an elastic material having a Shore hardness between 120 and 160.

6. A prosthetic foot as in claim 3, wherein the position of said snubber along said plantar member is approximately 3½ inches from said tertiary ball toward a heel of said foot.

7. A prosthetic foot as in claim 3, wherein the stiffness of said snubber is varied by altering the diameter of said snubber.

8. A prosthetic foot as in claim 1, wherein said primary ball has an aperture through its center capable of receiving an antirotational member, said primary socket has mating recesses on either side of the primary ball, and said antirotational member extends through said aperture of said primary ball into each of said recesses in said primary socket to pin said primary ball and said primary socket together and inhibit rotation of said primary ball with respect to said primary socket around all but one axis.

9. A prosthetic foot as in claim 8, wherein said antirotational member may be variably compressed by a threaded screw which is screwed into a threaded aperture cut longitudinally through said pylon above said primary ball containing said antirotational member in order to cause said antirotational member of become more rigid and resistant to motion.

10. A prosthetic foot as in claim 6, wherein said primary socket containing said primary ball is made more rigid by the addition of a cylindrical metal band surrounding said primary socket.

11. A prosthetic foot as in claim 2, wherein said plantar member and said dorsal member are constructed with a variable number of layers of unidirectional glass fiber cloth, the fibers of which said cloth running parallel to the length of said prosthetic foot and said cloth being embedded in a semirigid epoxy.

12. A prosthetic foot as in claim 1 wherein said adaptor assembly comprises an endoskeletal foot adaptor which fits over said pylon and is held in place on said pylon by a bolt and lock washer, said bolt being threaded into the pylon, said endoskeletal foot adaptor including a recess and an internal web.

13. A prosthetic foot as in claim 12, wherein said recess in said endoskeletal foot adaptor is filled with a molded elastic material extending slightly below the recess and forming an elastic cushion between said adaptor and said dorsal member to which said elastic material is bonded in a manner to cause elastic resistance to rotation of said adaptor with respect to said dorsal member and allows slight rotation of said prosthetic foot relative to a user's leg as necessary for simulation of natural walking.

14. A prosthetic foot as in claim 1, wherein said plantar member has wider heel and toe portions in respect to a narrower arch portion.

15. A prosthetic foot as in claim 1, wherein the center of said secondary ball is located above the center of said primary ball at a distance of approximately 20% of the length of the plantar member.

16. A prosthetic foot as in claim 1, wherein said plantar member is affixed to a cushioning layer along its entire bottom surface.

17. A prosthetic foot as in claim 1, wherein a cosmesis covers said foot.

18. A prosthetic foot as in claim 1, wherein said pylon is constructed from solid billets of high strength aluminum or titanium alloys.

19. A prosthetic foot as in claim 4, wherein said shear reducer member is at least partially made of an elastic material having a Shore hardness between 120 and 160.

20. A prosthetic foot, comprising:
    a flexible plantar member having first and second end portions wider in respect to a narrower central portion, said plantar member being constructed with a variable number of layers of unidirectional glass fiber cloth, the fibers of which said cloth run parallel to the length of said prosthetic foot, which said cloth is embedded in a semirigid epoxy, a primary socket connected to said plantar member adjacent said first end portion, said primary socket further positioned closely to a bottom horizontal surface of said plantar member, said primary socket having mating recesses on either of two opposite sides, at least one snubber member at least partially made of an elastic material having a Shore hardness between 120 and 160 adhesively attached to said plantar member at least one point between said first and second end portions of said plantar member, a shear reducer member at least partially made of an elastic material having a Shore hardness between 120 and 160 capable of reversibly contacting said dorsal member adjacent a secondary socket, said dorsal member connected to said plantar member at a point approximately midway between said primary socket and a tertiary ball connected to said plantar member adjacent said second end portion;

a rigid pylon having a first and second end, a primary ball attached to said first end of said pylon, said primary ball having an aperture through its center capable of receiving an antirotational member which extends through said aperture of said primary ball into each of said recesses in said primary socket to pin said primary ball and said primary socket together and inhibit rotation of said primary ball with respect to said primary socket around all but one axis, which antirotational member may be variably compressed by a threaded screw which is screwed into a threaded aperture cut longitudinally through said pylon above said primary ball containing said antirotational member in order to cause said antirotational member to become more rigid and resistant to motion, which said primary socket containing said primary ball is made more rigid by the addition of a cylindrical metal band surrounding said primary socket, a secondary ball attached to said pylon spaced from said primary ball at a distance of approximately 20% of the length of said plantar member, and an adaptor assembly attached to said second end of said pylon comprising an endoskeletal foot adaptor which fits over said pylon and is held in place on said pylon by a bolt and lock washer, said bolt being threaded into the pylon where said endoskeletal foot adaptor includes a recess and an internal web and where said recess in said endoskeletal foot adaptor is filled with a molded elastic material, said molded elastic material extending slightly below the recess and forming an elastic cushion between said adaptor and said dorsal member to which said elastic material is bonded, said elastic material being bonded in a manner to cause elastic resistance to rotation of said adaptor with respect to said dorsal member and to allow slight rotation of said prosthetic foot relative to a user's leg as necessary for simulation of natural walking, said pylon being connected to said plantar member by said primary socket engaging said primary ball;

said dorsal member having first and second end portions and being constructed with a variable number of layers of unidirectional glass fiber cloth, the fibers of which said cloth run parallel to the length of said prosthetic foot, said cloth being embedded in a semirigid epoxy, a secondary socket connected to said dorsal member adjacent said first end of said dorsal member, and a tertiary socket connected to said dorsal member adjacent said second end of said dorsal member, said dorsal member being connected to said pylon by said secondary ball engaging said secondary socket, and said dorsal member being connected to said plantar member by said tertiary socket engaging said tertiary ball; and, a cosmesis covering said foot.

* * * * *